(12) United States Patent
Tanimura et al.

(10) Patent No.: US 9,138,722 B2
(45) Date of Patent: Sep. 22, 2015

(54) METHOD FOR PRODUCING WATER-ABSORBENT RESIN PARTICLES

(71) Applicant: SUMITOMO SEIKA CHEMICALS CO., LTD., Harima-cho, Kako-gun, Hyogo (JP)

(72) Inventors: Kenji Tanimura, Himeji (JP); Hiroki Yabuguchi, Himeji (JP); Yuichi Onoda, Himeji (JP); Masayoshi Handa, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days.

(21) Appl. No.: 14/372,161

(22) PCT Filed: Jan. 22, 2013

(86) PCT No.: PCT/JP2013/051207
§ 371 (c)(1),
(2) Date: Jul. 14, 2014

(87) PCT Pub. No.: WO2013/128978
PCT Pub. Date: Sep. 6, 2013

(65) Prior Publication Data
US 2015/0158015 A1 Jun. 11, 2015

(30) Foreign Application Priority Data

Feb. 29, 2012 (JP) ................................. 2012-043571

(51) Int. Cl.
| | | |
|---|---|---|
| *B01J 20/30* | (2006.01) | |
| *C08F 2/32* | (2006.01) | |
| *C08F 20/06* | (2006.01) | |
| *C08F 120/06* | (2006.01) | |
| *A61L 15/12* | (2006.01) | |
| *B01J 20/26* | (2006.01) | |
| *C08L 33/02* | (2006.01) | |

(52) U.S. Cl.
CPC ............ *B01J 20/3085* (2013.01); *A61L 15/12* (2013.01); *B01J 20/262* (2013.01); *C08F 2/32* (2013.01); *C08F 20/06* (2013.01); *C08F 120/06* (2013.01); *C08L 33/02* (2013.01)

(58) Field of Classification Search
CPC ............ B01J 20/30; B01J 20/26; C08F 2/32; C08F 20/06; C08F 120/06; A61L 15/12; C08L 33/02

USPC .......... 525/243, 267, 298, 301, 255; 526/319, 526/287, 318.4; 524/318
See application file for complete search history.

(56) References Cited

U.S. PATENT DOCUMENTS

| | | | |
|---|---|---|---|
| 8,013,049 B2 | 9/2011 | Tanaka et al. | |
| 8,378,033 B2 * | 2/2013 | Handa et al. | ................... 525/267 |
| 8,415,433 B2 * | 4/2013 | Matsuzaki et al. | ............. 525/243 |
| 2009/0281247 A1 * | 11/2009 | Handa et al. | ................... 525/243 |
| 2010/0069592 A1 * | 3/2010 | Matzuaki et al. | ............. 526/287 |

FOREIGN PATENT DOCUMENTS

| | | |
|---|---|---|
| CN | 1461317 | 12/2003 |
| CN | 101466740 | 6/2009 |
| CN | 101479297 | 7/2009 |
| CN | 101835809 | 9/2010 |
| JP | 56-131608 | 10/1981 |
| JP | 7-070245 | 3/1995 |
| JP | 9-151224 | 6/1997 |
| JP | 10-057805 | 3/1998 |
| JP | 2008-037971 | 2/2008 |
| WO | 97/03114 | 1/1997 |
| WO | 2007/123188 | 11/2007 |
| WO | 2012/014748 | 2/2012 |
| WO | 2012/081355 | 6/2012 |

OTHER PUBLICATIONS

"Surfactant", Jun. 30, 1965, pp. 78-81 with an English translation.
Office Action issued in counterpart Chinese Patent Application No. 201380004689.9, mailed Mar. 31, 2015.

* cited by examiner

*Primary Examiner* — Michael M Bernshteyn
(74) *Attorney, Agent, or Firm* — Hamre, Schumann, Mueller & Larson, P.C.

(57) ABSTRACT

There is disclosed a method for producing water-absorbent resin particles comprising a step that includes reversed-phase suspension polymerization of a water-soluble ethylenically unsaturated monomer in a suspension containing a surfactant that comprises a surfactant that comprises a fatty acid ester of sorbitan or sorbitol, or derivative thereof, and a hydrocarbon dispersion medium. The fatty acid ester includes a lauric acid ester and at least one kind of other ester selected from the group consisting of palmitic acid esters, stearic acid esters and behenic acid esters. The proportion of the peak area for lauric acid ester is 30-60%, based on the total peak area for fatty acid esters in the GPC chromatogram obtained from the fatty acid esters, and the proportion of the total peak area for other ester is 10-50%.

2 Claims, No Drawings

METHOD FOR PRODUCING WATER-ABSORBENT RESIN PARTICLES

TECHNICAL FIELD

The present invention relates to a method for producing water-absorbent resin particles.

BACKGROUND ART

In recent years, water-absorbent resin particles are being applied in an even wider range of fields including hygienic materials such as disposable diapers and sanitary articles, agricultural materials such as water-retaining materials and soil conditioners, and industrial materials such as water blocking materials for cables and dew-catchers, as well as animal excreta treatment materials such as pet sheets and toilet formulations for dogs or cats, portable toilets, aromatic agents, absorbent drip sheets for meats, formulations for moisturizing cosmetics, and the like. Water-absorbent resin particles to be used for such application must have, for example, high water absorption capacity and an excellent water-absorption rate, as well as a median particle size suited for the application.

In the field of water blocking materials for cables, it is essential to rapidly arrest penetration of seawater. Also, forceful excretion of relatively large amounts of body fluids is an issue in fields of special hygienic materials such as adult diapers, incontinence pads, toilet-training pants and extra-high-absorbent napkins, pet sheets, portable toilets and the like. For such applications, particular attention has been directed toward improving absorption capacity and absorption rate. Absorption capacity can be adjusted by changing the amount of water-absorbent resin particles used in the absorbent article, but the absorption rate usually depends on the characteristic properties of the water-absorbent resin particles. Therefore, much research has therefore been carried out in the past with the aim of achieving an excellent water-absorption rate for water-absorbent resin particles.

However, reducing the particle size of water-absorbent resin particles to increase the water-absorption rate tends to impair their flow property and interfere with their handling as a powder. In addition, even if the water-absorption rate is excellent, if a relatively large number of coarse particles are present, i.e. if the particle size distribution is wide, the thickness tends to be non-uniform for water-absorbing articles whose thickness has been reduced. Because diffusion of water-absorbent resin particles is difficult and product thicknesses become non-uniform most notably with sheet-like articles that have water-absorbent resin particles sandwiched between nonwoven fabrics, such as with water blocking materials for cables, the particle size distribution of the water-absorbent resin particles should be as narrow as possible.

Examples of aqueous polymerization methods have been proposed as methods for increasing the water-absorption rate of water-absorbent resin particles while ensuring, a suitable particle size and a narrow particle size distribution, such methods including one in which a porous resin obtained in the presence of a foaming agent are crosslinked near the surface (see Patent Document 1), and one in which nitrogen air bubbles are introduced into a monomer comprising a fluorine-based surfactant for the polymerization (see Patent Document 2). Other proposals involve reversed-phase suspension polymerization, such as a method wherein a acrylic acid/acrylic acid salt water solution is subjected to reversed-phase suspension polymerization in the presence of a surfactant having an HLB value of 8 to 12 (see Patent Document 3), and a method of polymerizing a water-soluble ethylenically unsaturated monomer in the presence of water-absorbent resin particles with a different water-absorption rate (see Patent Document 4).

CITATION LIST

Patent Literature

Patent Document 1: WO97/003114
Patent Document 2: Japanese Patent Application Laid-open No. H10-57805
Patent Document 3: Japanese Patent Application Laid-open No. S56-131608
Patent Document 4: Japanese Patent Application Laid-open No. H9-151224

SUMMARY OF INVENTION

Technical Problem

The water-absorbent resin particles disclosed in Patent Documents 1 and 2 have not always been satisfactory in terms of both particle size and water-absorption rate performance.

With the water-absorbent resin particles disclosed in Patent Documents 3 and 4, it is possible to obtain somewhat excellent properties even from the standpoint of the water-absorption rate, despite the relatively large particle size, but the particle size distribution is still less than satisfactory.

Therefore, it is an object of the invention to provide a method whereby water-absorbent resin particles can be produced with a suitable particle size and a fast water-absorption rate, as well as a sufficiently narrow particle size distribution.

Solution to Problem

The invention relates to a novel method for producing water-absorbent resin particles, which is as follows.

1.

A method for producing water-absorbent resin particles, comprising a step that includes carrying out reversed-phase suspension polymerization of a water-soluble ethylenically unsaturated monomer in a suspension containing a surfactant that comprises a fatty acid ester of sorbitan, sorbitol or a derivative thereof, and a hydrocarbon dispersion medium,
  wherein the fatty acid ester includes a lauric acid ester and at least one kind of other ester selected from the group consisting of palmitic acid esters, stearic acid esters and behenic acid esters, and
  in a GPC chromatogram obtained from the fatty acid ester, the proportion of the peak area due to the lauric acid ester is 30-60% and the proportion of the total peak area due to the other ester is 10-50%, based on the total peak area due to the fatty acid esters.

2.

The method for producing water-absorbent resin particles according to 1., wherein the fatty acid ester is at least one selected from the group consisting of sorbitan fatty acid esters, polyoxyethylene sorbitan fatty acid esters, sorbitol fatty acid esters and polyoxyethylene sorbitol fatty acid esters.

Advantageous Effects of Invention

According to the invention it is possible to produce water-absorbent resin particles with a suitable particle size, as well as an excellent water-absorption rate and a sufficiently narrow particle size distribution. The water-absorbent resin particles obtained by the method of the invention have excellent handleability because of their narrow particle size distribution.

DESCRIPTION OF EMBODIMENTS

Preferred embodiments of the invention will now be described in detail. However, the present invention is not limited to the embodiments described below. All of the constituent elements described in the present specification may be employed in any combinations, such as are within the scope of the gist of the invention. For example, the numerical ranges for each of the properties may be established using the upper limits and lower limits for the numerical ranges described in the present specification, and any numerical values selected among the numerical values listed in the examples, as upper limits or lower limits.

The method for producing water-absorbent resin particles according to this embodiment comprises a step that includes reversed-phase suspension polymerization of a water-soluble ethylenically unsaturated monomer in a suspension containing a surfactant that comprises a fatty acid ester of sorbitan or sorbitol, or derivative thereof (hereunder also referred to simply as "sorbitan etc."), and a hydrocarbon dispersion medium. The fatty acid ester of the surfactant has a specific composition, as explained below.

The water-soluble ethylenically unsaturated monomer may be, for example, a nonionic monomer such as (meth)acrylic acid ("acrylic" and "methacrylic" will be collectively referred to throughout as "(meth)acrylic") and salts thereof, 2-(meth)acrylamide-2-methylpropanesulfonic acid and salts thereof (alkali salts), (meth)acrylamide, N,N-dimethyl (meth)acrylamide, 2-hydroxyethyl (meth)acrylate, N-methylol (meth)acrylamide and polyethylene glycol mono(meth) acrylate, or an amino group-containing unsaturated monomer such as N,N-diethylaminoethyl (meth)acrylate, N,N-diethylaminopropyl (meth)acrylate and diethylaminopropyl (meth) acrylamide, or quaternized form of the amino group-containing unsaturated monomer. The water-soluble ethylenically unsaturated monomer used may be at least one compound selected from the group mentioned above. From the viewpoint of industrial availability, the water-soluble ethylenically unsaturated monomer may be at least one compound selected from the group consisting of acrylic acid, methacrylic acid and salts thereof, acrylamide, methacrylamide and N,N-dimethylacrylamide. From the viewpoint of increased safety, the water-soluble ethylenically unsaturated monomer may be acrylic acid or methacrylic acid, or salts thereof. The water-soluble ethylenically unsaturated monomer may also include a bifunctional or greater monomer that functions as an internal-crosslinking agent.

The water-soluble ethylenically unsaturated monomer is usually supplied to the reversed-phase suspension polymerization in a form dispersed in the hydrocarbon dispersion medium, as a water solution. The concentration of the water-soluble ethylenically unsaturated monomer in the water solution may be in the range of 20 mass % to saturating concentration. Also, from the viewpoint of obtaining a satisfactory state of the W/O reversed-phase suspension and suitable particle size, and increasing the water absorption performance of the obtained water-absorbent resin particles, the concentration may be 25-50 mass %, 30-45 mass % or 35-42 mass %.

When the water-soluble ethylenically unsaturated monomer has an acid group such as (meth)acrylic acid and 2-(meth) acrylamide-2-methylpropanesulfonic acid, the acid group may be neutralized with an alkaline neutralizing agent such as an alkali metal salt. The alkaline neutralizing agent may be a water solution of sodium hydroxide, potassium hydroxide, ammonia, or the like. These alkaline neutralizing agents may be used alone or in combinations of two or more.

The neutralization degree by the alkaline neutralizing agent, with respect to the total acid group, may be 10-100 mol %, 30-90 mol %, 50-80 mol % or 60-78 mol %. If the neutralization degree is within this range, the permeating pressure of the obtained water-absorbent resin particles is increased, resulting in particularly high water-absorption performance. In addition, excess alkaline neutralizing agent does not easily remain in the water-absorbent resin particles, so that the safety can be further improved.

A radical polymerization initiator is usually added to a water solution of a water-soluble ethylenically unsaturated monomer. Examples of radical polymerization initiators include persulfuric acid salts such as potassium persulfate, ammonium persulfate and sodium persulfate; peroxides such as methyl ethyl ketone peroxide, methyl isobutyl ketone peroxide, di-t-butyl peroxide, t-butylcumyl peroxide, t-butyl peroxyacetate, t-butyl peroxyisobutyrate, t-butyl peroxypivalate and hydrogen peroxide; and azo compounds such as 2,2'-azobis(2-methylpropionamidine) dihydrochloride, 2,2'-azobis[2-(N-phenylamidino)propane]dihydrochloride, 2,2'-azobis[2-(N-allylamidino)propane]dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide] and 4,4'-azobis(4-cyanovaleric acid). Such radical polymerization initiators may be used alone, or two or more may be used in combination.

The amount of radical polymerization initiator added is usually 0.005 to 1 mol % with respect to the total moles of the water-soluble ethylenically unsaturated monomer. If the amount of radical polymerization initiator is less than 0.005 mol %, a long period of time tends to be required for the polymerization reaction. If the amount of radical polymerization initiator is greater than 1 mol %, abrupt polymerization reaction tends to take place.

The radical polymerization initiator may be combined with a reducing agent such as sodium sulfite, sodium hydrogen sulfite, ferrous sulfate and L-ascorbic acid, for use as a redox polymerization initiator.

A chain transfer agent may be added to the water solution of the water-soluble ethylenically unsaturated monomer to control the water absorption performance of the water-absorbent resin particles. Examples of such chain transfer agents include hypophosphorous acid salts, thiols, thiolic acids, secondary alcohols and amines.

A thickener may also be added to the water solution of the water-soluble ethylenically unsaturated monomer to alter the viscosity of the water solution. For a given stirring rotational speed, a higher viscosity of a water monomer solution generally results in a greater particle size of the water-absorbent resin particles. Examples of thickeners that may be used include at least one compound selected from the group consisting of hydroxyethyl cellulose, hydroxypropyl cellulose, methyl cellulose, carboxymethyl cellulose, polyacrylic acid, (partially) neutralized polyacrylic acid, polyacrylamide, polyethyleneimine, dextrin and sodium alginate. These may each be used alone, or in combinations of two or more.

In order to further improve the water absorption performance, such as the water-absorption rate, of the water-absorbent resin particles, a hydrophilic polymeric dispersion agent may be added to the water solution of the water-soluble ethylenically unsaturated monomer. Examples of hydrophilic polymeric dispersion agents that may be used include at least one compound selected from the group consisting of polyvinyl alcohol, polyvinylpyrrolidone, polyethylene glycol, polypropylene glycol, polyethylene glycol-polypropylene glycol block copolymer, polyglycerin, polyoxyethyleneglycerin, polyoxypropyleneglycerin, polyoxyethylene-polyoxypropylene glycerin copolymer and polyoxyethylene sorbitan fatty acid ester. These may each be used alone, or in combinations of two or more.

The surfactant comprises a fatty acid ester, which is an ester formed from sorbitan etc. and a fatty acid. Examples of such fatty acid esters include sorbitan fatty acid ester, polyoxyethylene sorbitan fatty acid ester, sorbitol fatty acid ester and polyoxyethylene sorbitol fatty acid ester. Among these, there may be used sorbitan fatty acid esters or polyoxyethylene sorbitan fatty acid esters, from the viewpoint of a satisfactory state of the W/O reversed-phase suspension, and more easily obtaining particles of a suitable form in the absorbent material with a suitable particle size and particle size distribution, and from the viewpoint of industrial availability. From the viewpoint of more easily obtaining water-absorbent resin particles with even more satisfactory properties, a sorbitan fatty acid ester may be used. These surfactants may be used alone or in combinations of two or more.

The fatty acid ester of sorbitan etc. are composed of a lauric acid ester, and at least one other ester selected from the group consisting of palmitic acid esters, stearic acid esters and behenic acid esters. The proportion of each fatty acid ester is calculated based on the peak area for each ester in the GPC chromatogram obtained by analyzing the fatty acid ester or surfactant by the analysis method described below. Specifically, the proportion of the peak area for lauric acid ester, based on the total peak area for sorbitan fatty acid esters in the GPC chromatogram is 30-60%, and the proportion of the total peak area for palmitic acid esters, stearic acid esters and behenic acid esters is 10-50%. Based on knowledge by the present inventors, this specific composition for the fatty acid esters can yield water-absorbent resin particles with a suitable particle size, as well as an excellent water-absorption rate and a sufficiently narrow particle size distribution. From the same viewpoint, the percentage of lauric acid ester may be 30-55%, 30-50% or 35-45%. The percentage of the total of palmitic acid esters, stearic acid esters and behenic acid esters may be 12-45%, 15-40% or 15-35%.

From the viewpoint of stabilizing the state of the W/O reversed-phase suspension, and using an efficient amount for a suspension-stabilizing effect, the amount of surfactant (especially sorbitan etc. fatty acid ester) used may be 0.1 to 5 parts by mass, 0.2 to 3 parts by mass or 0.4 to 2 parts by mass, with respect to 100 parts by mass of the water solution of the water-soluble ethylenically unsaturated monomer supplied for reversed-phase suspension polymerization.

In order to stabilize the state of the W/O reversed-phase suspension, a surfactant and a hydrophobic polymeric dispersion agent may be used in combination. The hydrophobic polymeric dispersion agent is usually dissolved in a hydrocarbon dispersion medium. Examples of hydrophobic polymeric dispersing agents include maleic anhydride-modified polyethylene, maleic anhydride-modified polypropylene, maleic anhydride-modified ethylene-propylene copolymer, maleic anhydride-modified EPDM (ethylene-propylene-diene terpolymer), maleic anhydride-modified polybutadiene, ethylene-maleic anhydride copolymer, ethylene-propylene-maleic anhydride copolymer, butadiene-maleic anhydride copolymer, oxidized polyethylene, ethylene-acrylic acid copolymer, ethyl cellulose and ethylhydroxyethyl cellulose. Among these, from the viewpoint of stability of the W/O reversed-phase suspension, there may be used at least one selected from the group consisting of maleic anhydride-modified polyethylene, maleic anhydride-modified polypropylene, maleic anhydride-modified ethylene-propylene copolymer, oxidized polyethylene and ethylene-acrylic acid copolymer. These hydrophobic polymeric dispersion agents may be used alone or in combinations of two or more.

The amount of hydrophobic polymer dispersing agent used may be 0.1 to 5 parts by mass, 0.2 to 3 parts by mass or 0.4 to 2 parts by mass, with respect to 100 parts by mass of the water solution of the water-soluble ethylenically unsaturated monomer supplied for reversed-phase suspension polymerization.

Examples of hydrocarbon dispersing medium include chain aliphatic hydrocarbons such as n-hexane, n-heptane, 2-methylhexane, 3-methylhexane, 2,3-dimethylpentane, 3-ethylpentane and n-octane; alicyclic hydrocarbons such as cyclohexane, methylcyclohexane, cyclopentane, methylcyclopentane, trans-1,2-dimethylcyclopentane, cis-1,3-dimethylcyclopentane and trans-1,3-dimethylcyclopentane; and aromatic hydrocarbons such as benzene, toluene and xylene. These hydrocarbon dispersing medium may each be used alone, or two or more may be used in combination. Among these hydrocarbon dispersing medium there may be used at least one compound selected from the group consisting of C7-8 chain aliphatic hydrocarbons and alicyclic hydrocarbons. From the viewpoint of a satisfactory state of the W/O reversed-phase suspension, and especially easily obtaining a suitable particle size of the water-absorbent resin particle for an excellent water-absorption rate, industrial availability, and stabilized quality, the hydrocarbon dispersion medium may also include n-heptane or cyclohexane. From the same viewpoint, a mixture of hydrocarbon dispersing medium may be used, such as the commercially available product EXXSOL Heptane (containing 75-85% n-heptane and isomeric hydrocarbons, product of ExxonMobil).

The amount of hydrocarbon dispersion medium used may be 50 to 650 parts by mass, 70 to 550 parts by mass or 100 to 450 parts by mass, with respect to 100 parts by mass of the water-soluble ethylenically unsaturated monomer supplied for reversed-phase suspension polymerization. If the amount of hydrocarbon dispersion medium used is less than 50 parts by mass, it may be difficult to control the polymerization temperature. If the amount of hydrocarbon dispersion medium is greater than 650 parts by mass, it may be difficult to increase productivity and economy may be impaired.

The temperature of the oil phase before suspension (the oily liquid) containing the hydrocarbon dispersion medium may be 50° C. or higher, 55° C. to 110° C., 60° C. to 100° C., 65° C. to 90° C. or 70° C. to 85° C.

The temperature of the suspension during the period from initial mixing of the hydrocarbon dispersion medium and the water solution comprising the water-soluble ethylenically unsaturated monomer, until the entire amount has been completely mixed, may be kept at 45° C. or higher, 50° C. to 100° C., 55° C. to 90° C., 60° C. to 85° C. or 65° C. to 80° C. If the temperature of the suspension is within this range during the mixing process, it is much easier to obtain a suitable particle size with a narrow molecular weight distribution.

After preparing the suspension by mixing the hydrocarbon dispersion medium and the water solution of the water-soluble ethylenically unsaturated monomer in the presence of the surfactant, the suspension may be heated if necessary, and be provided for reversed-phase suspension polymerization. The reaction temperature during reversed-phase suspension polymerization differs depending on the type of radical polymerization initiator used, and therefore cannot be specified for all cases. Usually, the reaction temperature may be 20° C.

to 110° C. or 40° C. to 90° C., from the viewpoint of promoting rapid polymerization and shortening the polymerization time, while also simplifying removal of polymerization heat and allowing a smooth reaction to take place. The reaction time is usually between 0.5 and 4 hours, although this is not limitative.

In most cases, the water-absorbent resin particles, or their water-containing gelated polymer as a precursor of the water-absorbent resin particles, are in various forms such as spherical, granular, fragmented or konpeito-shaped form, or an agglomerate thereof, as a result of the reversed-phase suspension polymerization. The water-containing gelated polymer may be granular, to more easily obtain a large specific surface area and a fast water-absorption rate, and it may be granular with uniform protrusions on the surfaces.

After the water-containing gelated polymer has been produced by reversed-phase suspension polymerization, a monomer water solution may be further added to the reaction mixture for a second reversed-phase suspension polymerization, and reversed-phase suspension polymerization may even be further repeated. The number of times that the reversed-phase suspension polymerization is repeated is not particularly restricted so long as it is two or more times, but it may be two or three times from the viewpoint of increasing productivity while maintaining suitable particle size and a narrow particle size distribution.

As a specific example, after the first reversed-phase suspension polymerization has been completed, the reaction mixture is cooled while appropriately adjusting the temperature, and then the water solution of the water-soluble ethylenically unsaturated monomer is added, suspending the water solution in an appropriately temperature-adjusted state if necessary, after which the second and subsequent reversed-phase suspension polymerizations are carried out.

The second and subsequent radical polymerization initiator and water-soluble ethylenically unsaturated monomer, added to the reaction mixture after the first reversed-phase suspension polymerization, may be the same type of compounds, in the same ranges of amounts, as used in the first polymerization. Also, the water solution of the water-soluble ethylenically unsaturated monomer may be either the same or different in the first, second and subsequent polymerizations.

The amount of water-soluble ethylenically unsaturated monomer used in the second and subsequent reversed-phase suspension polymerization may be 20 to 250 parts by mass, 40 to 200 parts by mass or 60 to 150 parts by mass with respect to 100 parts by mass of the first monomer. If the amount of water-soluble ethylenically unsaturated monomer added for the second and subsequent polymerizations is less than 20 parts by mass it may be difficult to achieve increased productivity, while if the amount added is greater than 250 parts by mass, the particle size of the obtained water-absorbent resin particles may become excessively large.

The concentration for the water solution of the second and subsequent water-soluble ethylenically unsaturated monomers may be at least 1 mass % or greater, 2-25 mass %, 3-20 mass % or 4-15 mass % higher than the concentration of the water solution of the first monomer, from the viewpoint of increased productivity.

The second and subsequent reversed-phase suspension polymerizations may be conducted under the same conditions as the first reversed-phase suspension polymerization.

The production method of this embodiment may further comprise, after the single or multiple reversed-phase suspension polymerizations, a step of removing a portion of the water of the produced water-containing gelated polymer (hereunder also referred to simply as "primary drying"). In the primary drying, the water content of the water-containing gelated polymer is adjusted to, for example, 20-130 mass % with respect to the water-soluble ethylenically unsaturated monomer component composing the water-containing gelated polymer.

There are no particular restrictions on the method for the primary drying, and it may be a method of externally heating the dispersion of the water-containing gelated polymer in the hydrocarbon dispersion medium for dewatering by azeotropic distillation, a method of removing the water-containing gelated polymer by decantation and performing reduced pressure drying, or a method of filtering out the water-containing gelated polymer with a filter and performing reduced pressure drying. For convenience of the production steps, the method of dispersing the water-containing gelated polymer obtained by polymerization in a hydrocarbon dispersion medium and performing dewatering by azeotropic distillation may be selected.

After the primary drying, post-crosslinking reaction may be carried out to crosslink the water-containing gelated polymer. Post-crosslinking reaction can further increase the water absorption performance of the water-absorbent resin particles.

The post-crosslinking agent used is a compound with two or more functional groups in the molecule that can react with a functional group in the water-soluble ethylenically unsaturated monomer (for example, a carboxyl group in the case of acrylic acid). The post-crosslinking agent may also be a water-soluble compound. Examples of post-crosslinking agents include polyols such as ethylene glycol, propylene glycol, 1,4-butanediol, trimethylolpropane, glycerin, polyoxyethylene glycol, polyoxypropylene glycol and polyglycerin; glycidyl ether compounds such as (poly)ethylene glycol diglycidyl ether, (poly)propylene glycol diglycidyl ether and (poly)glycerin diglycidyl ether; haloepoxy compounds such as epichlorohydrin, epibromohydrin and α-methylepichlorohydrin; diisocyanate compounds such as 2,4-tolylene diisocyanate and hexamethylene diisocyanate; oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol and 3-butyl-3-oxetaneethanol; oxazoline compounds such as 1,2-ethylene bisoxazoline; carbonate compounds such as ethylene carbonate; and hydroxyalkylamide compounds such as bis[N,N-di (β-hydroxyethyl)]adipamide. These may each be used alone or in mixtures of two or more.

Among these, glycidyl ether compounds may be selected from the viewpoint of excellent reactivity. From the viewpoint of high solubility in water and satisfactory handleability as a post-crosslinking agent, the post-crosslinking agent may be at least one compound selected from the group consisting of ethylene glycol diglycidyl ether, propylene glycol diglycidyl ether, glycerin diglycidyl ether, polyethylene glycol diglycidyl ether and polyglycerol glycidyl ether. From the viewpoint of obtaining high performance for the obtained water-absorbent resin particles, the post-crosslinking agent may be at least one compound selected from the group consisting of ethylene glycol diglycidyl ether and propylene glycol diglycidyl ether.

The amount of post-crosslinking agent added may be 0.0001 to 1 mol %, 0.0005 to 0.5 mol %, 0.001 to 0.1 mol % or 0.005 to 0.05 mol %, with respect to the total moles of the water-soluble ethylenically unsaturated monomer composing the water-containing gelated polymer. If the amount of post-crosslinking agent is less than 0.0001 mol % with respect to the total moles of the water-soluble ethylenically unsaturated monomer, crosslinking is weakened, and as a result the water-absorbent resin particle surfaces more readily increases in viscosity upon water absorption, thus tending to lower the water-absorption rate. If the amount of post-crosslinking agent is greater than 1 mol %, excessive crosslinking tends to result in lower water absorption capacity.

Mixture of the water-containing gelated polymer and the post-crosslinking agent can be accomplished after adjusting the water content of the water-containing gelated polymer to a specific range in the primary drying step. By thus controlling the water content at the time of mixture of the water-containing gelated polymer and the post-crosslinking agent, it is possible to more favorably promote the post-crosslinking reaction.

The water content of the water-containing gelated polymer in the post-crosslinking step may be 20-130 mass %, 25-110 mass %, 30-90 mass %, 35-80 mass % or 40-70 mass %, with respect to the water-soluble ethylenically unsaturated monomer component composing the water-containing gelated polymer. If the water content of the water-containing gelated polymer is within the aforementioned range, it is possible to shorten the primary drying step to increase efficiency, while maximizing the improvement in water absorption performance obtained by the post-crosslinking reaction.

The water content of the water-containing gelated polymer in the post-crosslinking step can be determined by calculating the ratio of the total of the amount obtained by subtracting the amount of the water externally extracted by the primary drying from the water amount in the monomer water solution before polymerization (the water amount after primary drying), and the amount of water used as necessary for addition of the post-crosslinking agent, with respect to the mass of the water-soluble ethylenically unsaturated monomer component composing the water-containing gelated polymer.

The mass of the water-soluble ethylenically unsaturated monomer component composing the water-containing gelated polymer can be determined by calculation as the theoretical polymer solid content, from the total mass of the water-soluble ethylenically unsaturated monomer used for polymerization reaction.

The mass ratio of the water amount of the gel after the primary drying and the amount of water to be used as necessary during addition of the post-crosslinking agent, may be 100:0 to 60:40, 99:1 to 70:30, 98:2 to 80:20 or 98:2 to 90:10, from the viewpoint of reasonably shortening the drying step for increased economy of the process, while uniformly dispersing the post-crosslinking agent.

In order to uniformly disperse the post-crosslinking agent during mixture of the water-containing gelated polymer and post-crosslinking agent, water or a hydrophilic organic solvent may be added as a solvent. Examples of hydrophilic organic solvents include lower alcohols such as methyl alcohol, ethyl alcohol and isopropyl alcohol, ketones such as acetone and methyl ethyl ketone, ethers such as dioxane and tetrahydrofuran, amides such as N,N-dimethylformamide, and sulfoxides such as dimethyl sulfoxide. These may each be used alone or in admixture with water as necessary, or two or more may be used in admixture.

The reaction temperature for post-crosslinking reaction of the water-absorbent resin particles with the post-crosslinking agent may be 60° C. or higher, 70° C. to 200° C. or 80° C. to 150° C. If the reaction temperature is less than 60° C., post-crosslinking reaction does not proceed as readily and an excessively long time tends to be necessary for reaction, while if the reaction temperature exceeds 200° C., the obtained water-absorbent resin particles may undergo degradation, potentially lowering the water absorption performance.

The reaction time for the post-crosslinking differs depending on the reaction temperature and the type and mixing amount of the post-crosslinking agent, and therefore cannot be specified for all cases, but usually it may be 1-300 minutes, or 5-200 minutes.

Following the post-crosslinking reaction, external energy such as heat may be applied to remove the water and hydrocarbon dispersion medium, by distillation or the like, for drying of the polymer (hereunder, this step will be referred to as "secondary drying"). Such secondary drying can yield powder-like water-absorbent resin particles with an excellent flow property.

There are no particular restrictions on the method for secondary drying, and for example, it may be a method of distilling a mixture of the polymer particles after post-crosslinking reaction, which are dispersed in the hydrocarbon dispersing medium, to simultaneously remove the water and hydrocarbon dispersing medium, a method of removing the polymer particles by decantation and performing reduced pressure drying, or a method of filtering out the polymer particles with a filter and performing reduced pressure drying. Among these, the method of distilling a mixture of the polymer particles after post-crosslinking reaction, which are dispersed in the hydrocarbon dispersion medium, in order to simultaneously remove the water and hydrocarbon dispersion medium, may be selected for convenience of the production steps.

Using the production method of this embodiment, it is possible to obtain water-absorbent resin particles with a suitable particle size and an excellent water-absorption rate, as well as a narrow particle size distribution and therefore excellent handleability as a powder.

The median particle size of the water-absorbent resin particles for this embodiment may be 100-600 μm. If the water-absorbent resin particles have this range of median particle size, it is possible to maintain their satisfactory handleability as a powder during the production of the absorbent material, and to reduce the thickness of the absorbent material. From the same viewpoint, the median particle size may be 110-500 μm, 120-400 μm or 130-350 μm.

The uniformity degree of the particle size of the water-absorbent resin particles may be 1.0-3.0. If the water-absorbent resin particles have this range of uniformity degree, it is possible to maintain their satisfactory handleability as a powder during the production of the absorbent material, and to reduce the thickness of the absorbent material. The uniformity degree may be between 1.2 and 2.8, or between 1.4 and 2.5. Measurement of the uniformity degree is described in detail in the examples which follow.

From the same viewpoint as for the uniformity degree, the proportion of particles of 500 μm over size, which remain on a 500 μm sieve, may be low in the particle size distribution of the water-absorbent resin particles as measured using standard sieves. Specifically, the proportion of particles of 500 μm over size may be no greater than 12 mass %, no greater than 10 mass % or no greater than 8 mass %.

The water-absorption rate of the water-absorbent resin particles for physiological saline may be 1-20 seconds. With such an excellent water-absorption rate, it is possible to prevent fluid leakage for use in an absorbent article. The water-absorption rate may be 1-15 seconds, 2-10 seconds, 2-8 seconds or 2-6 seconds. Measurement of the water-absorption rate is described in detail in the examples which follow.

There are no particular restrictions on the water absorption capacity of the water-absorbent resin particles for physiological saline, but since water-absorbent resin particles that absorb more water can further increase the absorption capacity of the absorbent article, it may be 30-90 g/g, 35-80 g/g, 45-75 g/g, 50-70 g/g or 55-65 g/g. Measurement of the water absorption capacity for physiological saline is described in detail in the examples which follow.

The water-absorbent resin particles may also contain additives such as a heat-resistant stabilizer, antioxidant, anti-bacterial agent or the like, depending on the purpose. The amount of such additives differs depending on the application of the water-absorbent resin particles, the types of additives, and other factors, but it may be 0.001 to 10 parts by mass, 0.01 to 5 parts by mass or 0.1 to 2 parts by mass with respect to 100 parts by mass of the water-absorbent resin particles.

EXAMPLES

The invention will now be explained in greater detail by examples and comparative examples. However, the present invention is not limited to the examples described below.

1. Analysis of Proportion of Each Fatty Acid Ester in Surfactant

Each of the surfactants used in the examples and comparative examples was weighed out to 100 mg in a vial, and 20 mL of tetrahydrofuran was added to dissolve the surfactant. The solution was filtered through a 0.45 μm PTFE filter to prepare a measuring sample. The measuring sample was analyzed by GPC under the conditions shown below. The total of the peak area values corresponding to each of the esters in the obtained chromatogram was recorded as an overall area value. The proportion of each ester was calculated from the ratio of the area value of each ester with respect to the overall area value.
  Apparatus: HLC-8320GPC (Tosoh Corp.)
  Column: TSKgel SuperH2500 (6.0 mmI.D.×15 cm)×4 (Tosoh Corp.)
  Detector: Differential refractometer (RI detector)
  Eluent: tetrahydrofuran
  Flow rate: 0.4 mL/min
  Column temperature: 40° C.
  Injection rate: 10 μL
  Calibration curve: polystyrene standard
  For sorbitan monolaurate (NONION LP-20R, product of NOF Corp.), the proportion of lauric acid ester was 64% and the total proportion of palmitic acid ester, stearic acid ester and behenic acid ester was 4%. For sorbitan monostearate (NONION SP-60R, product of NOF Corp.), the proportion of lauric acid ester was 1% and the total proportion of palmitic acid ester, stearic acid ester and behenic acid ester was 98%. The same analysis was conducted for the surfactants described in Examples 1 to 3 and Comparative Example 3, prepared by combining the two surfactants in the prescribed proportions. The proportion of each ester determined by analysis is shown in Table 1.

2. Preparation of Water-Absorbent Resin Particles

Example 1

There was prepared a round-bottom cylindrical separable flask with an inner diameter of 100 mm, equipped with a reflux condenser, a dropping funnel, a nitrogen gas inlet tube, and a stirrer. The stirrer used was an apparatus provided with a stirring blade with 4 slanted paddle blades with 50 mm blade diameters in two levels, and surface-coated with a fluorine resin. After placing 660 mL of n-heptane in the flask, there was added a surfactant, comprising a mixture of 0.99 g of sorbitan monolaurate (NONION LP-20R, product of NOF Corp.) and 0.11 g of sorbitan monostearate (NONION SP-60R, product of NOF Corp.), and the temperature was raised to 70° C. for dissolution of the surfactant.

Separately, 92 g (1.03 mol) of a 80.5 mass % acrylic acid water solution was placed in a 300 mL beaker and cooled with ice water while dropwise adding 147.7 g of a 20.9 mass % sodium hydroxide water solution for 75 mol % neutralization. Next, 0.10 g of potassium persulfate was added to dissolve it and prepare a monomer water solution. The polymer solid equivalent content of the monomer water solution was 91 g, and the water amount was 148.6 g.

The surfactant solution in the separable flask was stirred with the rotational speed of the stirrer set to 700 rpm, while adding the monomer water solution. After exchanging the system interior with nitrogen for 30 minutes, the flask was immersed in a water bath at 70° C. to raise the temperature, and polymerization reaction was conducted for 1 hour to produce a water-containing gelated polymer.

Next, an oil bath at 120° C. was used to raise the temperature, and the water and n-heptane were azeotropically distilled to remove 111.7 g of water out of the system under reflux of the n-heptane (primary drying). This was followed by addition of 4.14 g (0.00048 mol) of a 2% ethylene glycol diglycidyl ether water solution as a post-crosslinking agent. The water amount was 40.9 g, and the water content with respect to the water-soluble ethylenically unsaturated monomer component composing the water-containing gelated polymer (the polymer-based solid content) was 45 mass %. After adding the post-crosslinking agent, the mixture was kept at about 80° C. for 2 hours.

The n-heptane was then evaporated off for drying (secondary drying step) to obtain 88.2 g of granular water-absorbent resin particles.

Example 2

Granular water-absorbent resin particles, in an amount of 89.1 g, were obtained by the same procedure as Example 1, except that the surfactant was changed to a mixture of 0.77 g of sorbitan monolaurate (NONION LP-20R, product of NOF Corp.) and 0.33 g of sorbitan monostearate (NONION SP-60R, product of NOF Corp.).

Example 3

Granular water-absorbent resin particles, in an amount of 88.4 g, were obtained by the same procedure as Example 1, except that the surfactant was changed to a mixture of 0.66 g of sorbitan monolaurate (NONION LP-20R, product of NOF Corp.) and 0.44 g of sorbitan monostearate (NONION SP-60R, product of NOF Corp.).

Comparative Example 1

There was prepared a round-bottom cylindrical separable flask with an inner diameter of 100 mm, equipped with a reflux condenser, a dropping funnel, a nitrogen gas inlet tube, and a stirrer. The stirrer used was an apparatus provided with a stirring blade with 4 slanted paddle blades with 50 mm blade diameters in two levels, and surface-coated with a fluorine resin. After placing 660 mL of n-heptane into the flask, 1.10 g of sorbitan monolaurate (NONION LP-20R, product of NOF Corp.) was added as a surfactant, and the temperature was raised to 45° C. to dissolve the surfactant.

Separately, 92 g (1.03 mol) of a 80.5 mass % acrylic acid water solution was placed in a 300 mL beaker and cooled with ice water while dropwise adding 147.7 g of a 20.9 mass % sodium hydroxide water solution for 75 mol % neutralization. Next, 0.10 g of potassium persulfate was added to dissolve it and prepare a monomer water solution. The polymer solid equivalent content of the monomer water solution was 91 g, and the water amount was 148.6 g.

The surfactant solution in the separable flask was stirred with the rotational speed of the stirrer set to 700 rpm, while adding the monomer water solution. After exchanging the system interior with nitrogen for 30 minutes, the flask was immersed in a water bath at 70° C. to raise the temperature, and polymerization reaction was conducted for 1 hour to produce a water-containing gelated polymer. After polymerization, 0.41 g (0.000048 mol) of ethylene glycol diglycidyl ether was added and crosslinking reaction was carried out.

Next, an oil bath at 120° C. was used to raise the temperature, and the water and n-heptane were azeotropically distilled to remove 127.6 g of water out of the system under reflux of the n-heptane (primary drying). This was followed by addition of 5.52 g (0.00063 mol) of a 2% ethylene glycol diglycidyl ether water solution as a post-crosslinking agent. The water amount was 26.3 g, and the water content with respect to the water-soluble ethylenically unsaturated monomer component composing the water-containing gelated polymer (the polymer-based solid content) was 29 mass %. After adding the post-crosslinking agent, the mixture was kept at about 80° C. for 2 hours.

The n-heptane was then evaporated off for drying (secondary drying step) to obtain 87.4 g of granular water-absorbent resin particles.

Comparative Example 2

Spherical water-absorbent resin particles, in an amount of 89.1 g, were obtained by the same procedure as Comparative Example 1, except that the surfactant was changed to 1.10 g of sorbitan monostearate (NONION SP-60R, product of NOF Corp.).

Comparative Example 3

Spherical water-absorbent resin particles, in an amount of 90.3 g, were obtained by the same procedure as Example 1, except that the surfactant was changed to a mixture of 0.33 g of sorbitan monolaurate (NONION LP-20R, product of NOF Corp.) and 0.77 g of sorbitan monostearate (NONION SP-60R, product of NOF Corp.).

3. Evaluation

The water-absorbent resin particles obtained in the examples and comparative examples were evaluated in the following manner. The results are shown in Table 1.

(1) Water Absorption Capacity of Water-Absorbent Resin Particles, for Physiological Saline After placing 500 g of 0.9 mass % sodium chloride water solution (physiological saline) in a 500 mL beaker, 2.0 g of water-absorbent resin particles was added and the mixture was stirred for 60 minutes. The mass Wa (g) of a 75 µm-opening JIS standard sieve was measured first, and it was used for filtration of the beaker contents, after which the sieve was tilted to an inclination angle of about 30 degrees with respect to the horizontal and left to stand for 30 minutes, to filter out the excess water.

The mass Wb (g) of the sieve with the water-absorbing gel was measured, and the water absorption capacity was calculated by the following formula.

Water absorption capacity for physiological saline (g/g)=(Wb−Wa)/2.0

(2) Water-Absorption Rate of Water-Absorbent Resin Particles, for Physiological Saline This test was conducted in a room controlled to 25° C.±1° C. After measuring out 50±0.1 g of physiological saline into a 100 mL-volume beaker, a magnetic stirrer bar (8 mmϕ×30 mm, ringless) was loaded in and the beaker was immersed in a thermostatic bath to adjust the liquid temperature to 25±0.2° C. The beaker was then placed on the magnetic stirrer and a vortex was created in the physiological saline at a rotational speed of 600 rpm, upon which 2.0±0.002 g of water-absorbent resin particles were rapidly added to the physiological saline. A stopwatch was used to measure the time (sec) from addition of the water-absorbent resin particles until convergence of the vortex on the liquid surface, and the time was recorded as the water-absorption rate of the water-absorbent resin particles.

(3) Median Particle Size of Water-Absorbent Resin Particles

With 100 g of water-absorbent resin particles there was mixed 0.5 g of amorphous silica (product name: Sipernat 200, by Degussa Japan) as a lubricant.

For the measurement there were used 7 contiguous sieves among 13 different JIS standard sieves (openings: 1.7 mm, 1.4 mm, 850 µm, 600 µm, 500 µm, 355 µm, 250 µm, 180 µm, 150 µm, 106 µm, 75 µm, 45 µm and 38 µm).

The water-absorbent resin particles were placed in the sieve at the uppermost level among the sieves combined in the order of 500 µm, 355 µm, 250 µm, 180 µm, 150 µm, 106 µm and 75 µm, and a pan. A Ro-Tap shaker was then used for shaking of the sieves for 20 minutes.

Next, the mass of the water-absorbent resin particles remaining on each sieve was calculated as a percentage of the total mass, and upon adding up in order from the largest particle size, the relationship between sieve openings and the integrated value for the mass percentage remaining on the sieve was plotted on logarithmic probability paper. After connecting the plots on the probability paper with a straight line, the particle size corresponding to 50 mass % cumulative mass percentage was determined as the median particle size of the water-absorbent resin particles.

When either the mass percentage of water-absorbent resin particles remaining on the uppermost level sieve or lowermost level pan exceeded 15.9%, it was impossible to accurately assess the uniformity degree as explained below, and therefore 7 contiguous combinations were reselected among the sieves mentioned above, and the particle size distribution was remeasured such that the mass percentage of water-absorbent resin particles remaining on the uppermost level sieve and lowermost pan was no greater than 15.9%.

(4) Uniformity Degree of Particle Size Distribution

In measurement of the median particle size, the particle size (X1) corresponding to a cumulative mass percentage of 15.9 mass % and the particle size (X2) corresponding to one of 84.1 mass % were determined, and the uniformity degree was calculated by the following formula.

Uniformity degree=$X1/X2$

Specifically, a more narrow particle size distribution approaches a uniformity degree of 1, while a wider particle size distribution corresponds to a uniformity degree of greater than 1.

(5) Mass Percentage of Particles of Particle Size 500 µm Over Among Water-Absorbent Resin Particles (Percentage of 500 µm Over Particles)

In measurement of the median particle size, the total mass of particles remaining on the sieves with an opening of 500 µm or greater were calculated and divided by the mass of the water-absorbent resin particles supplied for the test, to determine the mass percentage of particles of 500 µm size over among the water-absorbent resin particles.

(6) Powder Handleability

The powder handleability for the water-absorbent resin particles of the examples and comparative examples was evaluated by five analysts having evaluated (1) to (4) above, based on the following criteria, and the most frequently selected evaluation was recorded as the powder handleability of the water-absorbent resin particles.

Good: Low dusting. Suitable flow property, facilitating procedures for weighing and cleaning.

Poor: High dusting. Low flow property, hampering procedures for weighing and cleaning.

TABLE 1

|  | Ester proportions in surfactant | | Water absorption capacity g/g | Water absorption rate sec | Median particle size μm | Uniformity degree | Mass Percentage of 500 μm over particles | Powder handleability Visual |
| --- | --- | --- | --- | --- | --- | --- | --- | --- |
|  | Lauric acid esters % | Palmitic acid esters, stearic acid esters and behenic acid esters % |  |  |  |  |  |  |
| Ex. 1 | 57 | 15 | 62 | 2 | 130 | 2.2 | 5 | Good |
| Ex. 2 | 45 | 32 | 61 | 3 | 130 | 2.3 | 6 | Good |
| Ex. 3 | 38 | 42 | 59 | 4 | 150 | 2.4 | 8 | Good |
| Comp. Ex. 1 | 64 | 4 | 65 | 2 | 130 | 3.2 | 13 | Good |
| Comp. Ex. 2 | 1 | 98 | 64 | 14 | 90 | 7.2 | 21 | Poor |
| Comp. Ex. 3 | 19 | 70 | 63 | 12 | 100 | 4.8 | 18 | Poor |

As seen in Table 1, the water-absorbent resin particles obtained in the examples all exhibited excellent water absorption performance including water-absorption rate, while also having suitable particle size, and also had narrow particle size distribution and therefore excellent powder handleability. On the other hand, the water-absorbent resin particles obtained in the comparative examples were inadequate in terms of the same performance.

Water-absorbent resin particles of the invention may be suitably used in a variety of fields, including: hygienic materials such as disposable diapers, sanitary articles and pet sheets; agricultural materials such as water-retaining materials and soil conditioners; and industrial materials such as water blocking materials for electric power and communication cables, and dew-catchers; and they may be most suitably used in fields including special hygienic materials such as adult diapers, incontinence pads, toilet-training pants and extra-high-absorbent napkins, and pet sheets, portable toilets, water-blocking materials for cables and the like.

The invention claimed is:

1. A method for producing water-absorbent resin particles, comprising a step that includes carrying out reversed-phase suspension polymerization of a water-soluble ethylenically unsaturated monomer in a suspension containing a surfactant that comprises a fatty acid ester of sorbitan, sorbitol or a derivative thereof, and a hydrocarbon dispersion medium, wherein the fatty acid ester includes a lauric acid ester and at least one kind of other ester selected from the group consisting of palmitic acid esters, stearic acid esters and behenic acid esters, and in a GPC chromatogram obtained from the fatty acid ester, the proportion of the peak area due to the lauric acid ester is 30-60% and the proportion of the total peak area due to the other ester is 10-50%, based on the total peak area due to the fatty acid esters.

2. The method for producing water-absorbent resin particles according to claim 1, wherein the fatty acid ester is at least one selected from the group consisting of sorbitan fatty acid esters, polyoxyethylene sorbitan fatty acid esters, sorbitol fatty acid esters and polyoxyethylene sorbitol fatty acid esters.

* * * * *